United States Patent [19]

Overland et al.

[11] Patent Number: 4,496,353

[45] Date of Patent: Jan. 29, 1985

[54] HOLLOW SURGICAL DISPOSABLE NEEDLE, PREFERABLY OF THE REDON TYPE

[76] Inventors: Christian Overland, L.O. Rasmussensvej 10, DK-3390 Hundested, Denmark; Knud-Werner Gaarde, Bakkegaardsvej 108, DK-3050 Humlebaek, Denmark

[21] Appl. No.: 416,371

[22] Filed: Sep. 9, 1982

[30] Foreign Application Priority Data

Sep. 11, 1981 [DK] Denmark ............... 4056/81

[51] Int. Cl.³ ............................................. A61M 27/00
[52] U.S. Cl. ..................................... 604/272; 604/280
[58] Field of Search ............ 604/48, 93, 264, 272–274, 604/280, 283, 161; 128/339

[56] References Cited

U.S. PATENT DOCUMENTS

| 354,018 | 12/1886 | Krieg | 128/339 |
|---|---|---|---|
| 1,131,155 | 3/1915 | Murphy | 128/339 |
| 3,181,336 | 5/1965 | Schofield | 604/274 |
| 3,596,658 | 8/1971 | Lange et al. | 604/161 |
| 3,674,014 | 7/1972 | Tillander | 604/264 |
| 3,788,320 | 1/1974 | Dye | 604/272 |
| 4,398,910 | 8/1983 | Blake et al. | 604/93 |

FOREIGN PATENT DOCUMENTS

| 219999 | 4/1910 | Fed. Rep. of Germany | 128/339 |
|---|---|---|---|
| 2335560 | 3/1974 | Fed. Rep. of Germany | 604/272 |

*Primary Examiner*—C. Fred Rosenbaum
*Assistant Examiner*—Michelle N. Lester
*Attorney, Agent, or Firm*—Cushman, Darby & Cushman

[57] ABSTRACT

A hollow surgical disposable needle of the Redon type and posteriorly surrounding and retaining a tube-shaped drain manufactured in one piece of a strip of stainless steel. This strip is bent into pipe-shape and pressed together at its front end in such a manner that the compressed part of the pipe comprises a cutting edge inclined relative to the longitudinal axis of the needle, whereas the pipe at its rear end comprises internal barbs securing the drain. In this manner an advantageous and very inexpensive Redon needle for disposable use is obtained.

7 Claims, 4 Drawing Figures

U.S. Patent  Jan. 29, 1985  4,496,353
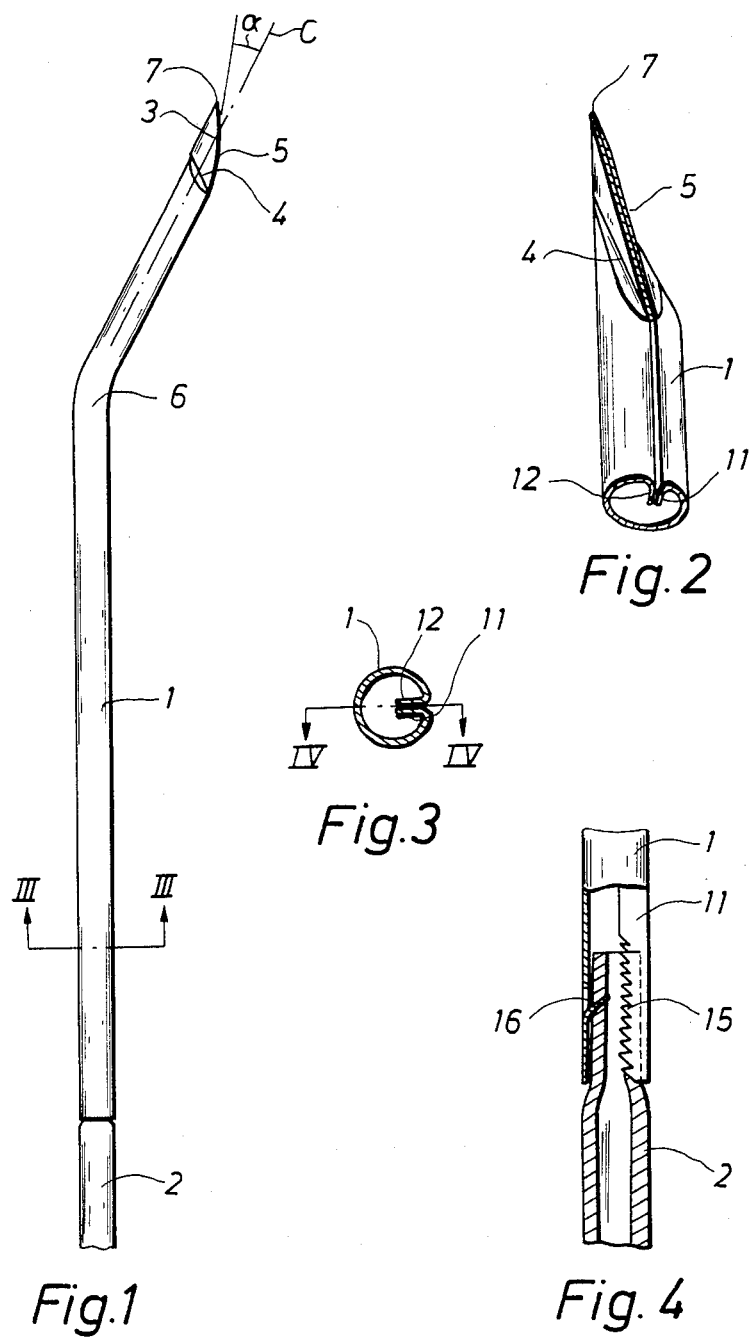

HOLLOW SURGICAL DISPOSABLE NEEDLE, PREFERABLY OF THE REDON TYPE

The invention relates to a hollow surgical disposable needle, preferably of the Redon type, and of the type anteriorly comprising a cutting edge inclined relative to the longitudinal axis of the needle and posteriorly surrounding and retaining a tube-shaped drain.

Redon needles are used during operations for the insertion of drains into the tissue of a wound area in order to drain said area. By the insertion, the skin is initially cut open whereafter the needle with the drain is pulled through the tissue and out through the skin, and when the drain is positioned the needle is removed.

The previously most frequently used Redon needles are solid needles manufactured of a solid piece with threads or grooves, over which the tubes are telescoped, cf. e.g. DE-OS No. 2,335,560. These needles are rather expensive and should therefore be reusable in order to be economically acceptable, which implies drawbacks concerning the cleaning and the sterilizing. Furthermore, the tube is not always firmly secured to the needle, and finally the needles are not bendable into the desired shape during the use, but must be manufactured with a curvature determined in advance. Usually the needles are manufactured with a pointed knife-like cutting edge permitting them to penetrate through the tissue.

Hollow needles are also known which are manufactured of metal pipes. A pointed front end is welded on these pipes and surrounds and retains the drain tube posteriorly by being pressed together thereabout. Such needles were intended for disposable use, but they are rather complicated and expensive to manufacture. Attempts have furthermore been made to manufacture the tube-shaped needle in one piece of a piping by compressing the front end of the pipe into a pointed closed end. However, such a point has no cutting effect, and the needle has gained no practical ground either.

The object of the invention is to provide a new surgical disposable needle of the above type, which partly retains the drain tube reliably, partly possesses good cutting properties, and finally which is inexpensive to manufacture.

The needle according to the invention is characterized in that the needle is manufactured in one piece and comprises a strip of plate-shaped material of an appropriate thickness and hardness bent into pipe shape, and that the pipe is pressed together and obliquely cut at its front end in such a manner that the compressed part forms an inclined edge, whereas the pipe at its rear end comprises internal barbs adapted to penetrate into the drain from the outside of said drain so as to firmly secure said drain in the needle. In this manner an inexpensive manufacture of the needle is obtained, partly since only a small amount of material is necessary and partly since an inexpensive manufacturing can be used. The oblique cutting edge permits an easy penetration of the needle through the tissue, and the internal barbs being pressed into the drain from the outside thereof ensure that the drain cannot be pulled out during the use.

According to a particularly advantageous embodiment of the needle according to the invention, the profile of the pipe-shaped needle is substantially circular-cylindrical, and its internal diameter is slightly smaller than the external diameter of the drain tube, whereas the external diameter of the needle is equal to or slightly greater than the external diameter of the drain tube. As a result, the profile of the needle corresponds to the profile of the drain tube, and the needle does not produce a larger opening than necessary for the insertion of the drain.

According to the invention the longitudinal side borders of the strip are sharply bent in such a manner that in the completely bent pipe they are located substantially parallel to each other and contacting each other, their free edges facing the centre of the pipe and preferably in such a manner that they extend to the centre of the pipe. In this manner the strip closes completely and forms a pipe obtaining an increased rigidity on account of the position of the free side borders.

A preferred embodiment of the needle according to the invention is shaped in such a manner that the compressed front part of the pipe is tightly compressed and forms a plane area substantially flushing with the bent side borders of the pipe. As a result, the front end of the pipe is reliably closed and the compressed part serves as the blade of a knife simultaneously contributing to a stiffening of the front end of the needle.

Furthermore according to the invention, the needle possesses particularly good cutting properties when the oblique edge resulting from the oblique cutting forms an angle with the longitudinal axis of the pipe situated in the area $10° < \alpha < 45°$, preferably in the area $15° < \alpha < 30°$, whereby a point is formed, and when both the oblique edge and especially the point are sharpened.

The needle may according to the invention be shaped in such a manner that the borderline between the compressed area and the pipe-shaped part extends substantially rectilinearly and intersects the longitudinal axis of the pipe under an angle of between 90° and 10°, preferably between 45° and 20°. In this manner the needles most appropriate for the required use may be chosen for various purposes.

Furthermore according to the invention, the needle may be shaped in such a manner that the internal barbs are preferably obliquely pointing forwards, and that they are formed by the sharply bent side borders of the bent strip by means of notches formed therein. As a result, the side borders of the strip are utilized in a simple manner for the shaping of the barbs simultaneously being provided with an advantageous shape. The barbs may, however, also be formed by preferably acute-angled portions partially punched out of the rear end of the strip.

According to the invention, the needle may be manufactured of stainless steel, a metal or an alloy, but other materials such as plastics may also be used.

The material used for the needle may have such a hardness and thickness that the needle achieves the necessary strength and that it is simultaneously possible to bend the needle by hand without using auxiliary tool and without the risk of breaking the needle. In this manner the needle is very applicable since it is easy to shape each needle with different desired curvatures.

The invention will be described below with reference to the accompanying drawing in which FIG. 1 illustrates a needle according to the invention, a drain tube being inserted, FIG. 2 is a perspective view of part of the front end with the cutting edge of the needle, FIG. 3 is a sectional view through the needle taken along the line III—III of FIG. 1, and FIG. 4 is a sectional view through the rear end of the needle taken along the line IV—IV of FIG. 3.

FIG. 1 illustrates a needle with a substantially pipe-shaped profile. This needle is manufactured in one piece by bending a strip of plate-shaped material in such a manner that the longitudinal side borders 11, 12 of the strip are bent towards the centre of the profile, cf. FIGS. 2, 3, and 4. At the rear end the needle 1 surrounds a bendable drain tube 2, and at the front end it is closed by means of a folded and compressed part 3 of the pipe. The compressed part 3 is substantially situated in a bisection plane of the pipe profile through the points of contact of the side borders 11 and 12 of the bent strip. The portion of the compressed part including the side borders 11 and 12 is cut off along a line before, during or after the compression. This line forms an angle $\alpha$ with the longitudinal axis C in such a manner that the compressed part 3 is defined by an oblique edge 5 and at its free end possesses a point 7. The angle $\alpha$ is in the area between 10° and 45°, preferably between 15° and 30°. The oblique edge 5 and the point 7 are sharpened, e.g. by grinding. The borderline 4 between the compressed part 3 and the pipe-shaped part of the needle 1 is rectilinearly illustrated in the drawing, but it may also curve. This borderline intersects the longitudinal axis of the pipe under an angle of between 90 and 10°, referably between 45° and 20°. The most frequently used shape of the needle is illustrated in FIG. 1, viz. with a bending 6 flushing with the compressed part 3, but besides the needle may be bent in hand as desired. FIG. 2 is a sectional view of the front end of a needle with a particulary acute defining between the compressed part 3 and the pipe-shaped part of the needle. This embodiment has proved to be particularly advantageous.

In order to permit the pipe to receive the circular-cylindrical drain tube 2, said pipe is preferably substantially circular-cylindrically shaped, cf. FIG. 3, but besides it may have other shapes too.

FIG. 4 is a sectional view of the partly intersected rear end of the needle. It illustrates the side border 11 sharply bent inwards of the strip and comprising barbs 15 pointing forwards. At the bending of the pipe about the drain tube 2 inserted therein, these barbs are pressed into the side wall of the drain tube in such a manner that the drain tube 2 is not withdrawn from the needle during the use. Partially punched and preferably acute-angled portions 16 bent inwards may be provided in the rear end of the strip as barbs.

For the manufacture of the needle stainless steel or a metal or an alloy is preferably used, a material preferably being chosen which possesses such a hardness and such a thickness that the needle possesses the necessary strength and so that it is simultaneously possible to bend the needle by hand without using auxiliary tool.

We claim:

1. A disposable surgical needle to be used for drawing a flexible drain catheter into a body comprising:
    an elongated strip of material having longitudinal edges and forming a tubular shaped needle body,
    the longitudinal edges abutting each other along the length of the needle body and extending generally radially inwardly from the peripheral edge of the needle body,
    the anterior end of the needle body having a flat planar section extending through and parallel to the abutting longitudinal edges,
    the planar portion having an edge extending diagonally to the longitudinal axis of the tubular needle body and defining a cutting edge, the posterior end being capable of receiving the catheter.

2. A disposable surgical needle according to claim 1 wherein the posterior end of the needle body is adapted to surround the drain catheter and has barb-like projections extending inwardly toward the anterior end to retain the catheter.

3. A disposable surgical needle according to claim 1 wherein the needle body is substantially cylindrical.

4. A disposable surgical needle according to claim 1 wherein the cutting edge forms an angle to the longitudinal axis of the needle body between 10° and 45°.

5. A disposable surgical needle according to claim 1 wherein the cutting edge is curved.

6. A disposable surgical needle according to claim 1 wherein the needle body is manually bendable without risk of breakage.

7. A one-piece surgical disposable needle for drawing a flexible catheter into and through a body, said needle comprising an elongated metal strip having a width dimension and a length dimension and having opposite longitudinal border portions and shaped to form a tubular needle body having a curved side wall said border portions being in abutment with each other over substantially their entire width and extending generally radially inwardly to about the center of the tubular needle body, said tubular needle body being shaped at one end into a planar portion by compression of the body side wall, said planar portion having a cutting edge extending obliquely to the axis of said tubular needle body and terminating in a point, the opposite end of said needle body being adapted to surround a catheter and the inwardly facing edges of said border portions of said strip having notches therein for aiding in gripping a catheter.

* * * * *